(12) United States Patent
Lee et al.

(10) Patent No.: US 10,548,780 B1
(45) Date of Patent: Feb. 4, 2020

(54) APPARATUS FOR INFORMING EXCRETIONS AND CONTROL METHOD THEREOF

(71) Applicant: Littleone Inc., Gwangju (KR)

(72) Inventors: Byung Kyu Lee, Seoul (KR); Byung Hee Yun, Seoul (KR)

(73) Assignee: LITTLEONE INC., Gwangju (KR)

( * ) Notice: Subject to any disclaimer, the term of this patent is extended or adjusted under 35 U.S.C. 154(b) by 0 days.

(21) Appl. No.: 16/198,395

(22) Filed: Nov. 21, 2018

(30) Foreign Application Priority Data

Aug. 24, 2018 (KR) ........................ 10-2018-0099173

(51) Int. Cl.
   *A61L 15/56* (2006.01)
   *A61F 13/42* (2006.01)
   *A61F 13/84* (2006.01)

(52) U.S. Cl.
   CPC ........ *A61F 13/42* (2013.01); *A61F 2013/421* (2013.01); *A61F 2013/424* (2013.01); *A61F 2013/8482* (2013.01)

(58) Field of Classification Search
   None
   See application file for complete search history.

(56) References Cited

U.S. PATENT DOCUMENTS

| 2013/0110064 | A1* | 5/2013 | Richardson | A61F 13/49 604/361 |
| 2014/0350502 | A1* | 11/2014 | Berland | A61F 13/42 604/361 |
| 2015/0356852 | A1* | 12/2015 | Estrada | A61F 13/42 340/584 |
| 2019/0091073 | A1* | 3/2019 | Wen | A61F 13/42 |

FOREIGN PATENT DOCUMENTS

KR   10-2016-0077373 A   7/2016

* cited by examiner

*Primary Examiner* — Brent Swarthout

(57) ABSTRACT

Disclosed are an excrement alarming apparatus and an excrement alarming method, the excrement alarming apparatus includes: a temperature sensor provided on one side of the excrement alarming apparatus and configured to measure temperature; a humidity sensor provided on one side of the excrement alarming apparatus and configured to measure humidity; a controller configured to detect excrement using temperature information measured by the temperature sensor, first humidity information measured by the humidity sensor, and second humidity information received from an external device; and a communication unit configured to transmit an excrement detection signal indicative of the detection of the excrement.

9 Claims, 7 Drawing Sheets

APPARATUS FOR INFORMING EXCRETIONS AND CONTROL METHOD THEREOF

CROSS-REFERENCE TO RELATED APPLICATIONS

This application claims priority to Korean Patent Application No. 10-2018-0099173 filed on Aug. 24, 2018 in Korea, the entire contents of which are hereby incorporated by reference in their entirety.

BACKGROUND OF THE INVENTION

Field of the Invention

The present invention relates to an excrement alarming apparatus attached to a diaper and the like, and more particularly to an excrement alarming apparatus for detecting excrement such as feces and urine and alarms the detection of the excrement, and a control method thereof.

Related Art

A diaper is a product filled in perineum to receive excrements such as feces and urine, and the diaper is usually made from a material which has an excellent absorbing capability and can be dried quickly. However, despite the absorbing and drying capabilities of the diaper, if a user's skin is exposed to ammonia from urine and bacteria from faces for a long period of time, the user is more likely to develop dermatitis. For this reason, a pee mark has been recently inserted into a lower side of a diaper so that a user can check excrement more easily. However, even a diaper having the peek mark is used, a user needs to frequently check excrement. Thus, if a user is far from a subject (a person who is wearing a diaper), it is difficult to immediately respond to excrement while the user is asleep or the like.

To solve this problem, Korean Patent Application Publication No. 10-2016-0077373 (Publication Date: Jul. 4, 2016) discloses a "smart diaper management system" in which a user device wirelessly receives information on the presence of feces and urine from a terminal attached to a diaper and displays the received information, so that information on time, a frequency, and a period as well as the presence of the feces and urine is provided. However, this kind of method depends simply on detection indicators of a sensor to determine the presence of feces and urine, and hence, if ambient temperature and humidity are changed due to a weather condition, the presence of feces and urine may not be detected or may be detected wrongly.

SUMMARY OF THE INVENTION

The present invention is to provide an excrement alarming apparatus capable of accurately detecting excrement, regardless of a change in a surrounding environment, and a control method thereof.

The present invention is to provide an excrement alarming apparatus capable of reducing power consumption and a control method thereof.

In one general aspect of the present invention, there is provided an excrement alarming apparatus including: a temperature sensor provided on one side of the excrement alarming apparatus and configured to measure temperature; a humidity sensor provided on one side of the excrement alarming apparatus and configured to measure humidity; a controller configured to detect excrement using temperature information measured by the temperature sensor, first humidity information measured by the humidity sensor, and second humidity information received from an external device; and a communication unit configured to transmit an excrement detection signal indicative of the detection of the excrement.

The temperature sensor and the humidity sensor may, when attached to a diaper, measure temperature and humidity of the diaper, respectively.

The controller may be further configured to determine that excrement is detected, when a differential value between the second humidity information and the first humidity information is greater than a first threshold value and a variation of temperature information measured within a preset period of time is greater than a second threshold value.

The second humidity information may be determined based on location information of the external device or measured by a humidity sensor provided in the external device.

The second humidity information may be included in a payload of an advertising packet that is transmitted from the external device before paring between the excrement alarming apparatus and the external device.

The controller may set a weight for at least one of the first threshold value or the second threshold value based on at least one of information on reference humidity, location information, date information, weather information, or time information.

In another general aspect of the present invention, there is provided an excrement alarming method implemented by an excrement alarming apparatus, the method comprising: generating first humidity information using a humidity sensor provided on one side of the excrement alarming apparatus, and receiving second humidity information from an external device; comparing a differential value between the first humidity information and the second humidity information with a first threshold value; when the differential value between the first humidity information and the second humidity information is greater than the first threshold value, comparing a variation of temperature information measured by a temperature sensor, which is provided on one side of the excrement alarming apparatus, within a preset period of time with a second threshold value; and when the variation of the temperature information is greater than the second threshold value, transmit an excrement detection signal indicating that excrement is detected.

In yet another general aspect of the present invention, there is provided an application installed in a user device, including: a code configured to receive temperature information and humidity information from an excrement alarming apparatus; a code configured to determine reference humidity based on at least one of the humidity information or information acquired from the user device; and a code configured to, when excrement is detected based on the temperature information, the humidity information, and information on the reference humidity, alarm the detection of excrement through the user device.

In yet another general aspect of the present invention, there is provided an excrement alarming apparatus including: a temperature sensor provided on one side of the excrement alarming apparatus and configured to measure temperature; at least one humidity sensor provided on one side of the excrement alarming apparatus and configured to measure humidity; a controller configured to determine reference humidity based on humidity information measured by the at least one humidity sensor, and detect excrement using temperature information measured by the temperature sensor, the humidity information measured by the at least one humidity sensor, and information on the reference humidity; and a communication unit configured to transmit an excrement detection signal indicative of the detection of the excrement.

DESCRIPTION OF EXEMPLARY EMBODIMENTS

Figure 1:
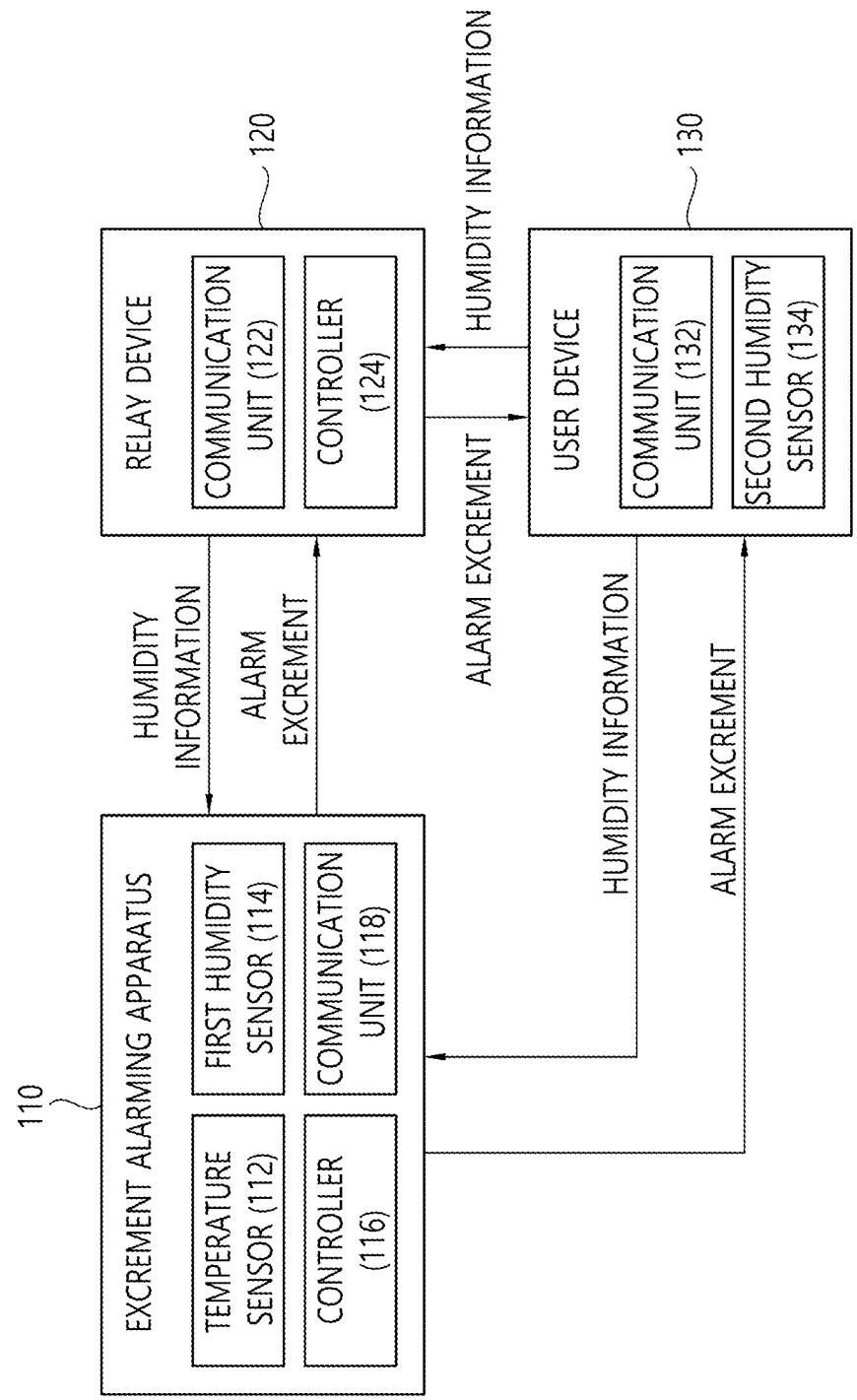
FIG. 1 is a diagram illustrating an excrement alarming system according to an embodiment of the present invention.

Hereinafter, embodiments of the present invention will be described in detail with reference to the accompanying drawings in such a manner that the technical idea of the present invention may easily be carried out by a person with ordinary skill in the art to which the invention pertains. The present invention may, however, be embodied in different forms and should not be construed as limited to the embodiments set forth herein. In the drawings, anything unnecessary for describing the present invention will be omitted for clarity, and also like reference numerals in the drawings denote like elements.

In addition, in the entire specification, when an element is referred to as "including" another element, the element should not be understood as excluding other elements so long as there is no special conflicting description, and the element may include at least one other element.

FIG. 1 is a diagram illustrating an excrement alarming system according to an embodiment of the present invention.

Hereinafter, an excrement alarming system according to a first embodiment is described. Referring to FIG. 1, an excrement alarming system according to an embodiment of the present invention may include an excrement alarming apparatus 110, a relay device 120, and a user device 130.

The excrement alarming apparatus 110 may be attached to a product, such as a diaper, required to detect the presence of excrement and may alarm the detection of the excrement through the relay device 120, the user device 130, etc. To this end, the excrement alarming apparatus 110 may include a temperature sensor 112, a first humidity sensor 114, a controller 116, and a communication unit 118. In FIG. 1, the temperature sensor 112, the first humidity sensor 114, the controller 116, and the communication unit 118 are exemplarily illustrated as individual components, but the temperature sensor 112, the first humidity sensor 114, the controller 116, and the communication unit 118 may be implemented as one integrated circuit, when necessary.

The temperature sensor 112 and the first humidity sensor 114 may be provided on one side of the excrement alarming apparatus 110 to measure temperature and humidity, respectively. For example, when the excrement alarming apparatus 110 has a rear surface attachable to a lower side of a diaper, the temperature sensor 112 and the first humidity sensor 114 may be provided on the rear surface of the excrement alarming apparatus 110 to measure temperature and humidity of the lower side of the diaper.

The controller 116 may detect the presence of excrement using temperature information measured by the temperature sensor 112, first humidity information measured by the first humidity sensor 114, and second humidity information received from an external device such as the relay device 120 and the user device 130.

For example, when the controller 116 receives the second humidity information from an external device through the communication unit 118, the controller 116 may set the second humidity information as reference humidity for detection of excrement. To this end, the excrement alarming apparatus 110 and the relay device 120 and/or the user device 130 may perform short-range wireless communication. Here, the second humidity information may be included in a broadcasting signal from the relay device 120 and/or the user device 130 before paring between the excrement alarming apparatus 110 and the relay device 120 and/or the user device 130, or may be included in a signal transmitted from the relay device 120 and/or the user device 130 after paring between the excrement alarming apparatus 110 and the relay device 120 and/or the user device 130. The controller 116 may determine reference humidity using a humidity sensor embedded in the excrement alarming apparatus 110 when the controller 116 is set not to receive the second humidity information from an external device or the second humidity information is not received from an external device within a preset period of time.

If the reference humidity is determined in this procedure, the controller 116 may calculate a differential value between reference humidity information and first humidity information measured by the first humidity sensor 114. If the differential value between the reference humidity information and the first humidity information is greater than a first threshold, the controller 116 may determine that excrement is possibly present. In this case, the controller 116 may compare a variation of temperature information measured by the temperature sensor 112 within a preset period of time with a second threshold. In this case, when a variation of temperature information measured by the temperature sensor 112 is greater than the second threshold, the controller 116 may determine that excrement is detected. Here, the first threshold may be, for example, 10% to 20%, and the second threshold may be 3° C. to 5° C.

In the case where the first humidity information measured by the first humidity sensor 114 is determined as reference humidity, when ambient temperature and humidity are changed due to a season and weather, the system may determine such change as a result of excrement and thereby a wrong excrement alarming signal may occur. In addition, in the case where a threshold (a first threshold and a second threshold) for detection of excrement is set as a fixed value, the presence of excrement may not be detected as a variation of humidity and/or temperature fails to reach the corresponding threshold even when the excrement is present in a high or low humidity and/or temperature environment, or a wrong alarming signal may be generated as a variation of humidity and/or temperature exceeds the corresponding to the threshold even when there is no excrement. The excrement alarming apparatus 110 according to the present invention may set humidity information acquired by an external device as reference humidity and set a weight for at least one of the first threshold or the second threshold based on at least one of information on the reference humidity, location information, date information, weather information, or time information, thereby accurately alarming excrement despite a change in a surrounding environment.

When excrement is detected by the controller 116, the communication unit 118 may generate an excrement detection signal indicating that the excrement is detected, and transmit the excrement detection signal. In addition, the communication unit 118 may transmit temperature information and/or humidity information measured by the temperature sensor 112 and/or the first humidity sensor 114 to the relay device 120 and/or the user device 130. To this end, the communication unit 118 may be implemented as a short-range wireless communication module, such as a lower-power Bluetooth Low Energy (BLE) module. In addition, the communication unit 118 may include a Wireless Fidelity (Wi-Fi) module to secure a wider communication range.

Meanwhile, the relay device 120 serves to relay communication the excrement alarming apparatus 110 and the user device 130, and may include a communication unit 122 and a controller 124.

The communication unit 122 may transmit a signal received from the communication unit 118 of the excrement alarming apparatus 110 to the user device 130, or transmit a signal received from the user device 130 to the excrement alarming apparatus 110. To this end, the communication unit 122 may include a short-range wireless communication module such as Bluetooth and a Wi-Fi module. For example, communication between the excrement alarming apparatus 110 and the relay device 120 may be BLE, and communication between the user device 130 and the relay device 120 may be Wi-Fi.

The controller 124 may convert a signal received from the excrement alarming apparatus 110 into a format enabled to be transmitted to the user device 130, and convert a signal received from the user device 130 into a format enabled to be transmitted to the excrement alarming apparatus 110.

Meanwhile, although not illustrated in FIG. 1, a humidity sensor may be embedded even in the relay device 120. In this case, the relay device 120 may transmit humidity information measured by the embedded humidity sensor to the excrement alarming apparatus 110 through the communication unit 122. In this case, the excrement alarming apparatus 110 may set humidity information measured by the relay device 120 as reference humidity.

The user device 130 may be a device for monitoring excrement of a user to which the excrement alarming apparatus 110 is attached, and may include an application 132 and a second humidity sensor 134. The user device 130 may be implemented as a mobile wireless communication device, in which the application 132 for alarming excrement, such as a smart phone, a table PC, and a smart watch, can be installed.

The application 132 may include: a first code for receiving temperature information and humidity information measured by the excrement alarming apparatus 110 through a communication unit (not illustrated) of the user device 130; a second code for recording temperature information, humidity information, excrement alarming information, etc. measured by the excrement alarming apparatus 110 in a memory (not illustrated) of the user device 130; a third code for determining reference humidity based on at least one of humidity information measured by the excrement alarming apparatus 110 or information acquired by the user device 130; a fourth code for transmitting information on reference humidity to the excrement alarming apparatus 110; a fifth code for confirming whether an excrement detection signal is received from the excrement alarming apparatus 110; and a sixth code for, when the excrement detection signal is confirmed, alarming detection of excrement through the user device 130. For example, the third code may be configured to determine humidity information acquired based on location information of the user device as reference humidity, to determine humidity information set by a user as reference humidity, or to determine humidity information measured by the second humidity sensor 134 provided in the user device 130 as reference humidity. Here, the location information of the user device may be acquired by a Global Positioning System (GPS) module embedded in the user device 130. The location information of the user device 130 may be utilized to determine reference humidity only in the case where the second humidity sensor 134 is not provided in the user device 130. In the case where the second humidity sensor is not provided in the user device 130, the application 132 may request humidity information of a corresponding location from a server (not illustrated) based on a GPS signal acquired by the GPS module of the user device 130, and may determine the humidity information acquired by the request as reference humidity information.

Figure 2:
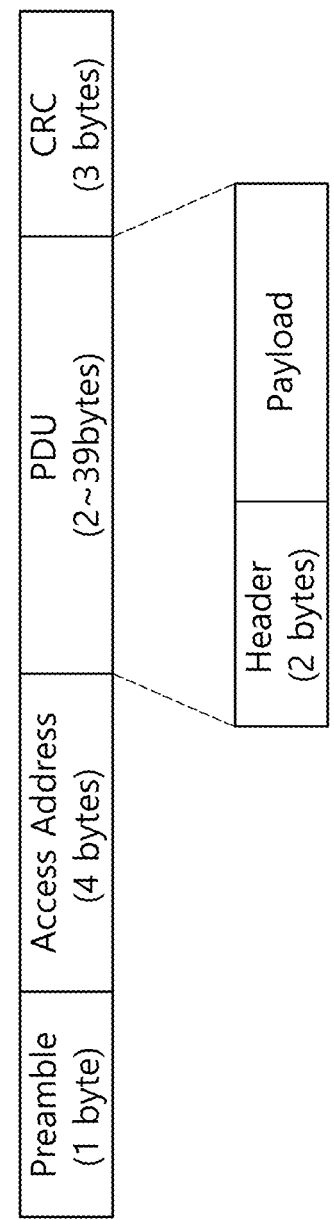
FIG. 2 is a diagram illustrating a packet structure according to an embodiment of the present invention.

FIG. 2 is a diagram illustrating a packet structure according to an embodiment of the present invention.

An excrement alarming apparatus according to the present invention may, for example, communicate with a relay device and/or a user device using the packet structure illustrated in FIG. 2. The packet structure illustrated in FIG. 2 may be a structure of an advertising packet broadcasted before the apparatus and the relay device and/or the user device are connected, that is, before the devices have yet to be established.

For example, the advertising packet in the structure as illustrated in FIG. 2 may be used when a user uses a plurality of excrement alarming apparatuses. Generally, short-range wireless communication, such as Bluetooth, may operate based on one-to-one connection. In the case where a user have a first excrement alarming apparatus and a second excrement alarming apparatus, when the user device is paired with the first excrement alarming apparatus, communication between the second excrement alarming apparatus and the user device is not enabled. In this case, the user device may not receive information from the second excrement alarming apparatus, and thus, although the second excrement alarming apparatus detects excrement, the second excrement alarming apparatus is not able to immediately alarm the detection of the excrement to the user. However, an advertising packet as illustrated in FIG. 2 may be broadcasted from each device without paring between devices, and therefore, when information is transmitted through the advertising packet, a plurality of unspecific devices in the surroundings may receive information properly.

Referring to FIG. 2, an advertising packet according to an embodiment of the present invention may include a preamble, an access address, a Packet Data Unit (PDU), and a Cyclical Redundancy Check (CRC).

The preamble is for synchronization between devices for communication and may consist of 1 byte. The access address is for connection in the link layer and may consist of 4 bytes. The PDU is for information transmission and may consist of a header and a payload. The header may have a fixed length of 2 bytes, and the payload may contain a variety of information by a length instructed by length information included in the header. The PDU may consist of 2 bytes at minimum and 39 bytes at maximum. The CRC is for detection of a data error and may be consist of 3 bytes.

For example, when the user device transmits humidity information to an excrement alarming apparatus, the header of the PDU includes an indicator of 1 bit indicating transmission of the humidity information, and length information about humidity information, and the payload may include a value indicative of the humidity information, and information on Identification (ID) of the excrement alarming apparatus.

In another example, when the excrement alarming apparatus transmits temperature information and humidity information to the user device and/or the relay device, the header of the PUD includes a 1-bit indicator indicative of transmission of the humidity information and a 1-bit indicator indicative of transmission of temperature information, and the payload may contain a value indicative of the humidity information, a value indicative of the temperature information, and information on ID of the excrement alarming apparatus.

In another example, when the excrement alarming apparatus transmits an excrement detection signal to a user device and/or a relay device, the header of the PDU may be included in an indicator indicative of excrement detection signal, and information on ID of the excrement alarming apparatus, and the number of times excrement has been detected in a preset period of time.

Figure 3:
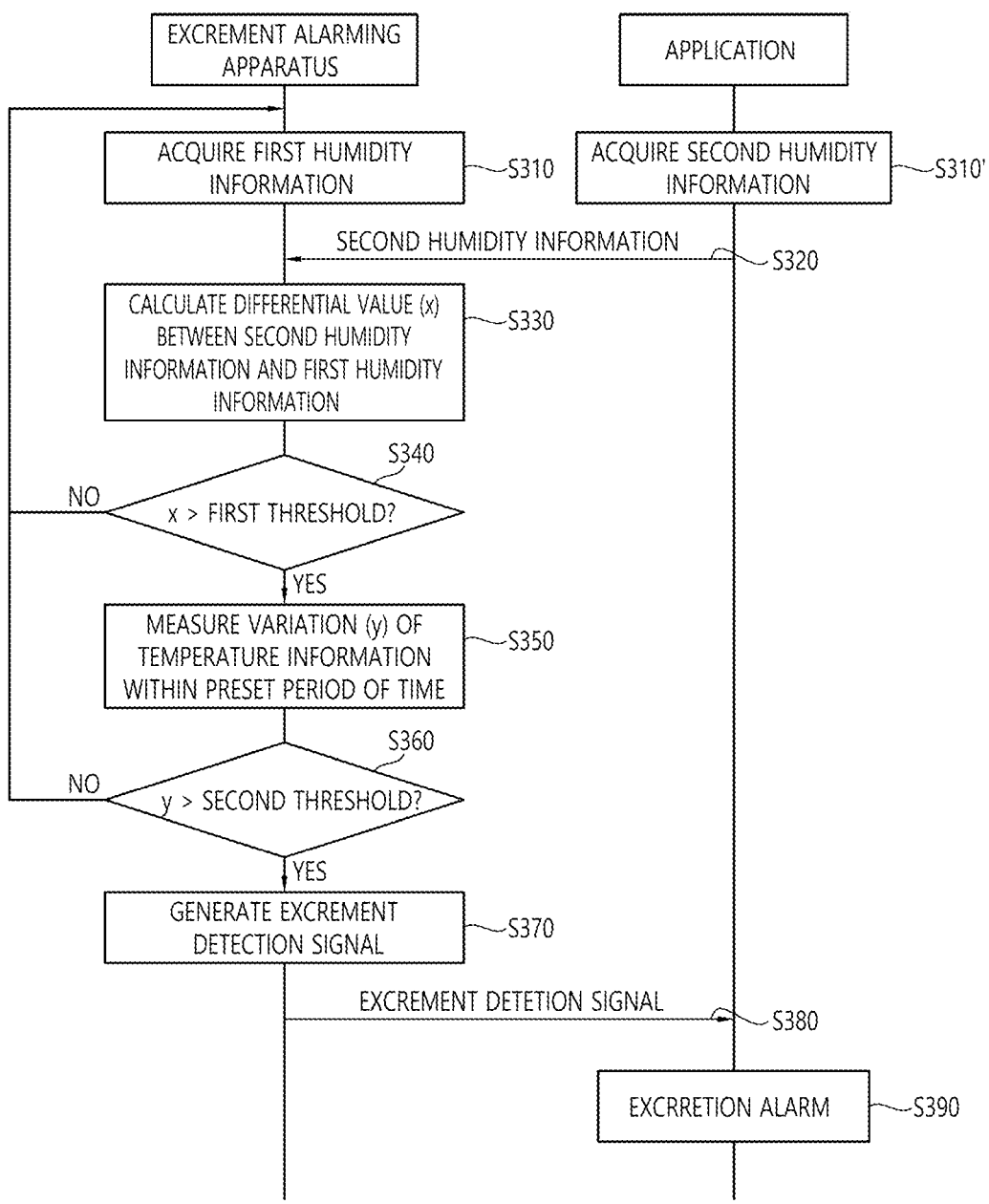
FIG. 3 is a flowchart illustrating an excrement alarming method according to an embodiment of the present invention.

FIG. 3 is a flowchart illustrating an excrement alarming method according to an embodiment of the present invention.

Hereinafter, an excrement alarming apparatus according to the first embodiment of the present invention is described with reference to FIG. 3. In FIG. 3, communication between an excrement alarming apparatus and an application is exemplarily illustrated, but the excrement alarming apparatus may communicate not just with the application, but also with a relay device in the same manner shown in FIG. 3. In this case, the relay device may transmit an excrement detection signal to the application.

Referring to FIG. 3, the excrement alarming apparatus may periodically acquire first humidity information from a humidity sensor (S310). In this case, even the application may periodically acquire second humidity information based on location information of the user device or acquire second humidity information from a humidity sensor (S310'). When the second humidity information is acquired, the application may transmit the second humidity information to the excrement alarming apparatus using the packet structure illustrated in FIG. 2 (S320).

When the second humidity information is received, the excrement alarming apparatus may calculate a differential value x between first humidity information and the second humidity information (S330) and compare the differential value x with a first threshold value (S340). When the differential value x is equal to or smaller than the first threshold value, the excrement alarming apparatus may determine that excrement is not present. However, when the differential value x is greater than the first threshold value, the excrement alarming apparatus may measure a variation y (S350) by calculating a differential value of temperature information measured a temperature sensor within a preset period of time, and compare the variation y with the second threshold value (S360). When the variation y is greater than the second threshold value, the excrement alarming apparatus may generate an excrement detection signal indicative of detection of excrement (S370), and transmits the generated excrement detection signal (S380). In this case, the excrement alarming apparatus may set a weight for at least one of the first threshold value or a second threshold value based on at least one of information on reference humidity, location information, date information, weather information, or time information.

For example, in the case where the first threshold value is set to 10%, date information of the current location corresponds to summer, and weather information corresponds to raining, the excrement alarming apparatus may reset the first threshold value to 5% by assigning a weight to the first threshold value. In the case where the first threshold value is not reset but maintained at 10%, if ambient humidity is 95% in a raining environment in summer, a value of x cannot exceed the first threshold value of 10% as long as humidity information of 105% is not measured by a humidity sensor of the excrement alarming apparatus, and therefore, the excrement alarming apparatus does not operate. On the contrary, if a user moves to a room where a humidifier is operating while ambient humidity is 30% in a clean environment in winter, the humidity may be changed by 10% or more, and in this case, the excrement alarming apparatus may reset the first threshold value to 20%, thereby preventing a wrong alarm. Here, the location information of the excrement alarming apparatus, the current date information, the weather information, and the time information may be acquired by a user device and/or the relay device.

Meanwhile, the excrement alarming apparatus may transmit an excrement detection signal after paring with a user device in which an application is installed, or may transmit an excrement detection signal before pairing with an external device (the user device or the relay device). A method for transmitting an excrement detection signal using an advertising packet may be used when a user has a plurality of excrement alarming apparatuses.

When the application receives the excrement detection signal from the excrement alarming apparatus and/or the relay device, the application may provide an excrement alarm to the user through a display, an LED, a speaker, a vibration motor, etc. of a user terminal (S390).

Figure 4:
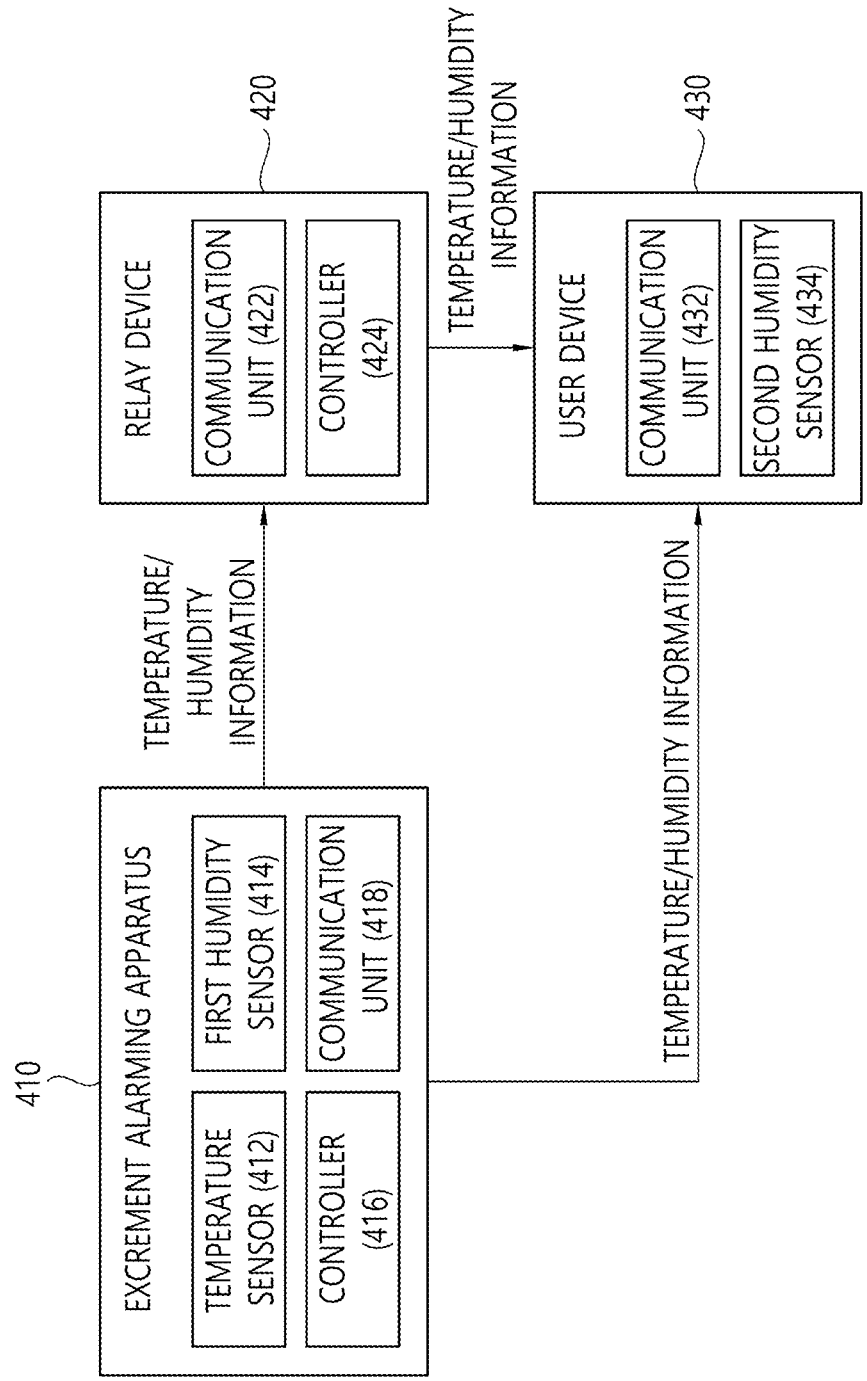
FIG. 4 is a diagram illustrating an excrement alarming system according to another embodiment of the present invention.

FIG. 4 is a diagram illustrating an excrement alarming system according to another embodiment of the present invention.

Hereinafter, an excrement alarming apparatus according to a second embodiment is described. The second embodiment is different from the first embodiment in that an application detects excrement. The excrement alarming apparatus detects excrement in the first embodiment, and thus, even in the case where the excrement alarming apparatus is not able to transmit an excrement detection signal since a user is located at a remote distance from a non-user, the excrement alarming apparatus is able to provide an excrement alarm to the user by itself or through the relay device. On the other hand, in the second embodiment, since an application detects excrement, the excrement alarming apparatus consumes less power to detect excrement, and thus, the excrement alarming apparatus may be used for a longer period of time without replacing or recharging a battery of the excrement alarming apparatus.

Referring to FIG. 4, an excrement alarming apparatus 410 may include a temperature sensor 412, a first humidity sensor 414, a controller 416, and a communication unit 418. The temperature sensor 412, the first humidity sensor 414, and the communication unit 418 are identical to the excrement alarming apparatus 110 of the first embodiment in terms of configuration/operation, and thus, a detailed description thereof is herein omitted.

The controller 416 may perform control to periodically transmit temperature information periodically measured by the temperature sensor 412 and first humidity information periodically measured by the first humidity sensor 414 to a relay device 420 and/or a user device 430. In addition, when a temperature and/or humidity information request is received through the communication unit 418, the controller 416 may perform control such that temperature and/or information is transmitted in a corresponding cycle in response to the request.

The temperature information and/or the humidity information measured by the excrement alarming apparatus 410 may be broadcasted to the relay device 420 and/or the user device 430.

The relay device 420 may include a communication unit 422 and a controller 424. Basic configuration and operation of the relay device 420 may be similar to those of the relay device 420 according to the first embodiment. However, when an application for alarming excrement is installed, the relay device 420 may serve as the user device 430.

The user device 430 may include an application 432 and a second humidity sensor 434. The application 432 may be configured to include: a first code for receiving temperature information and first humidity information measured by the excrement alarming apparatus 410; a second code for recording the temperature information, the first humidity information, etc. received from the excrement alarming apparatus 410; a third code for determining reference humidity based on at least one of the first humidity information or information acquired by the user device 430; a fourth code for comparing a differential value between the first humidity information and information on the reference humidity with a first threshold value; a fifth code for, when the differential value between the first humidity information and the information on the reference humidity is greater than the threshold value, comparing a variation of temperature information measured within a preset period of time with a second threshold value; a sixth code for, when the variation of the temperature information is greater than the second threshold value, determine that excrement is detected; a seventh code for alarming detection of excrement through the user device 430; and an eighth code for setting a weight for at least one of the first threshold value or the second threshold value based on at least one of location information of the user device 432, date information, weather information, or time information.

For example, the first code may be configured to acquire the temperature information and/or the first humidity information from a payload of an advertising packet received before paring between the user device 430 and the excrement alarming apparatus 410. The third code may be configured to determine humidity information acquired based on the location information of the user device 430 as reference humidity, determine humidity information set by a user as reference humidity, or determine the second humidity information measured by the second humidity sensor 434 of the user device 430 as reference humidity. Alternatively, the third code may be configured to determine an average value of a plurality of humidity information received from the excrement alarming apparatus 410 within a preset period of time as reference humidity.

Figure 5:
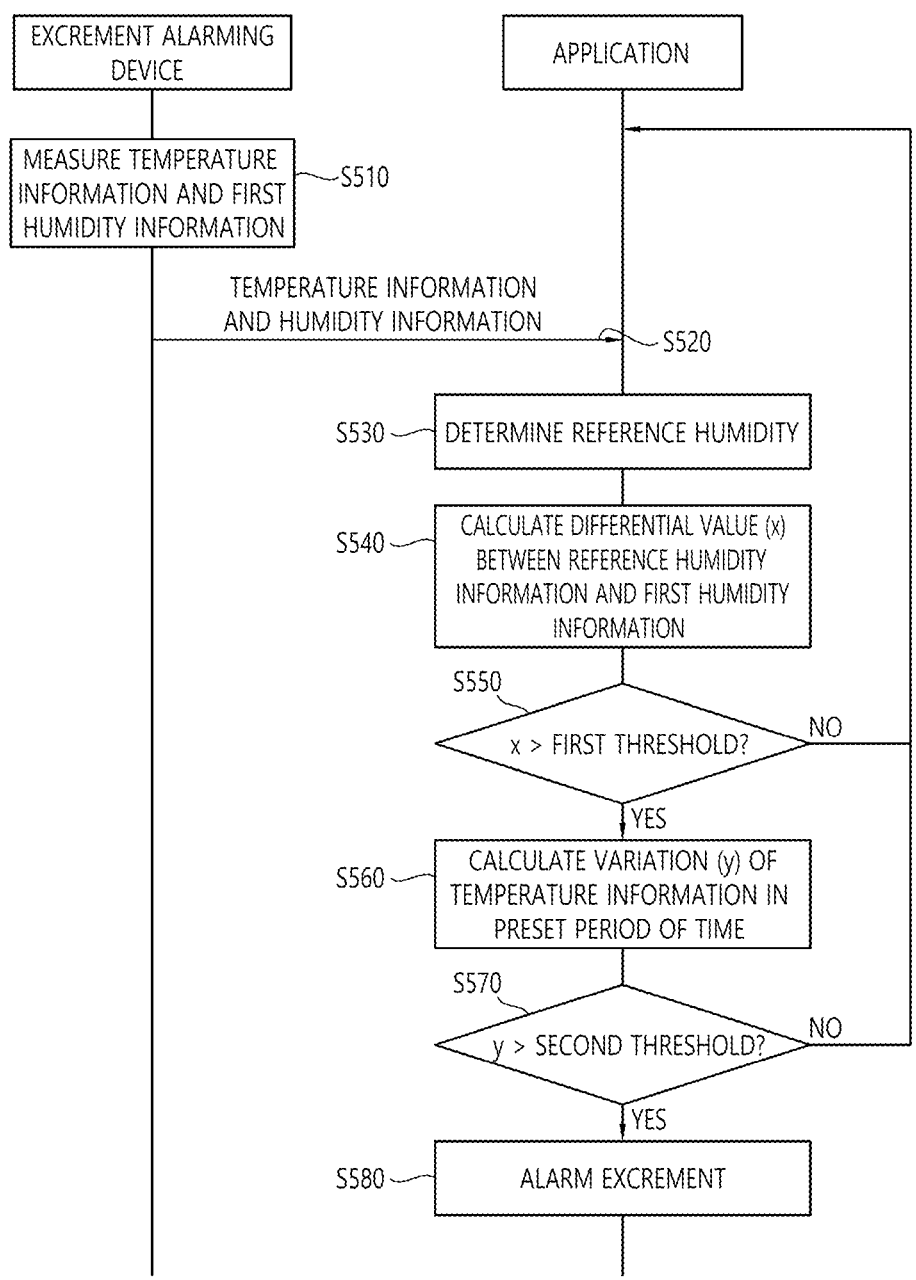
FIG. 5 is a flowchart illustrating an excrement alarming method according to another embodiment of the present invention.

FIG. 5 is a flowchart illustrating an excrement alarming method according to another embodiment of the present invention.

Hereinafter, an excrement alarming method according to a second embodiment of the present invention is described with reference to FIG. 5.

The excrement alarming apparatus may periodically measure temperature information and/or humidity information (S510), and transmit the measured information to a user device and/or a relay device through the packet structure as illustrated in FIG. 3 (S520).

The user device and/or the relay device may determine reference humidity based on first humidity information received from the excrement alarming apparatus, humidity information acquired based on location information of the user device and/or the relay device, humidity information set by a user, and second humidity information measured by a humidity sensor provided in the user device and/or the relay device (S530).

When the reference humidity is determined, the application calculates a differential value x between the first humidity information and information on the reference humidity (S540), and compare the differential value x with the first threshold value (S550). When the differential value x is equal to or smaller than the first threshold value, the application may repeatedly calculate the differential value x at a cycle in which information is received from the excrement alarming apparatus. When the differential value x is greater the first threshold value, the application calculates a variation y of temperature information measured within a preset period of time (S560), and compare the variation y with a second threshold value (S560). When the variation y is equal to or smaller than the second threshold value, the application may determine that excrement is not detected and may monitor whether new temperature information and humidity information is received from the excrement alarming apparatus. When the variation y is greater than the second threshold value, the application may determine that excrement is detected, and may provide an excrement alarm to a user through the user device and/or the relay device (S580).

Figure 6:
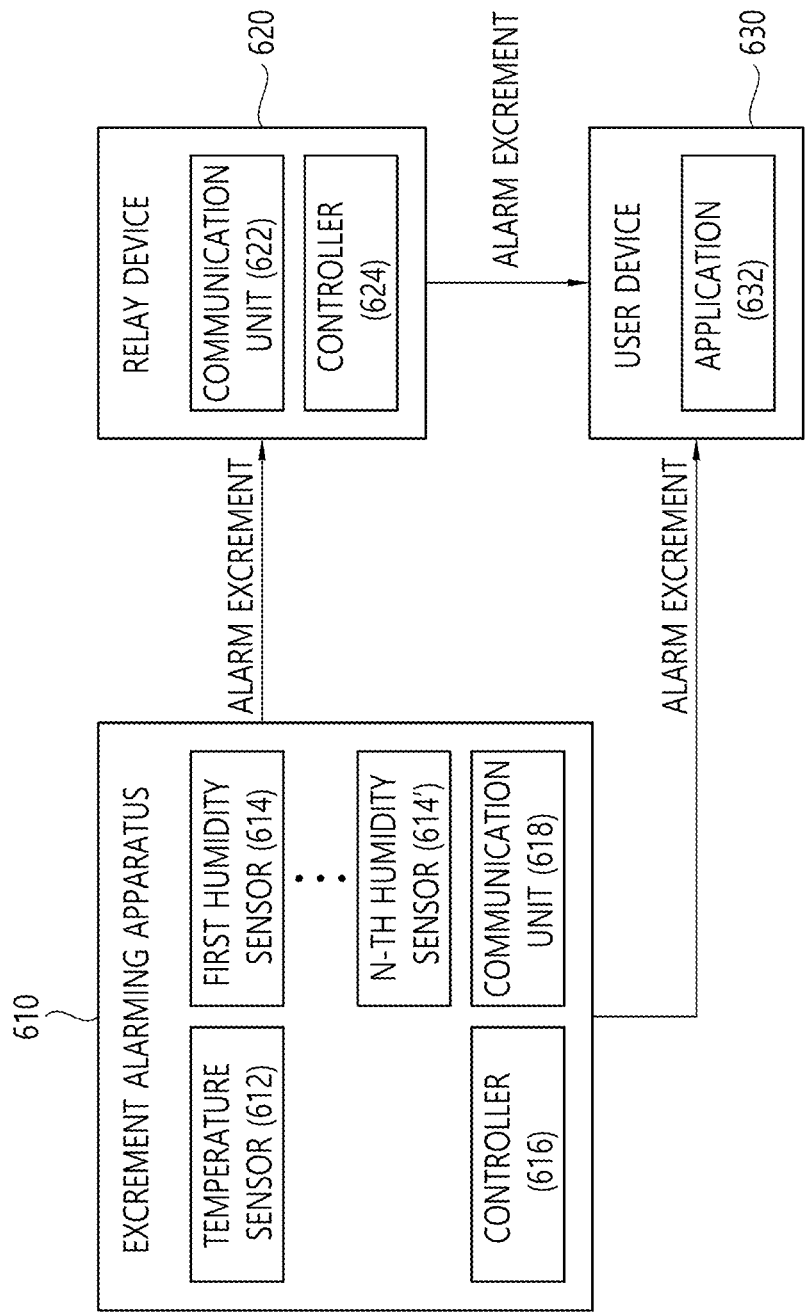
FIG. 6 is a diagram illustrating an excrement alarming system according to another embodiment of the present invention.

FIG. 6 is a diagram illustrating an excrement alarming system according to another embodiment of the present invention.

Hereinafter, an excrement alarming system according to a third embodiment of the present invention is described. The third embodiment may be utilized when an excrement alarming apparatus 610 is not allowed to receive information on reference humidity from a relay device 620 and/or a user device 630 or when the excrement alarming apparatus 610 includes a plurality of humidity sensors 614 and 614'.

Referring to FIG. 6, the excrement alarming apparatus 610 may include temperature sensor 612, at least one humidity sensor 614 and 614', a controller 616, and a communication unit 618.

The temperature sensor 612 and the first humidity sensor 614 may be provided on one side of the excrement alarming apparatus 610 to measure temperature and humidity, respectively.

The controller 616 may determine reference humidity based on humidity information measured by the at least one humidity sensor 614 and 614'. In addition, the controller 616 may detect excrement using temperature information measured by the temperature sensor 612, humidity information measured by the at least one humidity sensor 614 and 614', and information on reference humidity. For example, when the reference humidity is determined, the controller 616 may compare a differential value between information on the reference humidity and humidity information measured by the first humidity sensor 614 with a first threshold value. When the differential value between the information on the reference humidity and the humidity information measured by the first humidity sensor 614 is greater than the first threshold value, the controller 616 may compare a variation of temperature information measured by the temperature sensor 612 within a preset period of time with a second threshold value. When the variation of the temperature information is greater than the second threshold value, the controller 616 may determine that excrement is detected. In this case, the controller 616 may determine an average value of temperature information measured by the at least one humidity sensor 614 and 614' within a preset period of time as reference humidity.

For example, when the excrement alarming apparatus 610 include one humidity sensor, the controller 616 may set an average value of humidity information measured by a corresponding humidity sensor within a preset period of time as reference humidity. In this case, the controller 610 may reset the reference humidity in a predetermined cycle so as to operate adaptively in response to a change in a surrounding environment. For example, the predetermined period may be a period in which a timer of the excrement alarming apparatus 610 expires. Alternatively, when a differential value between humidity information measured by a humidity sensor and the reference humidity does not reach a first threshold value but instead falls into a predetermined range, the controller 616 may reset the reference humidity.

In another example, when the excrement alarming apparatus 610 includes a plurality of humidity sensors, the controller 616 may determine reference humidity using humidity information measured by a second humidity sensor provided on the other side of the excrement alarming apparatus 610. In this case, a humidity sensor provided on one side of the excrement alarming apparatus 610 may measure humidity of a diaper, and a humidity sensor provided on the other side of the excrement alarming apparatus 610 may measure ambient humidity. Even in this case, the reference humidity may be reset periodically.

When excrement is detected by the controller 616, the communication unit 618 may construct an excrement detection signal and transmit the excrement detection signal to the relay device 620 and/or the user device 630. Even in this case, a packet structure as the same as that illustrated in FIG. 2 may be used.

When a controller 624 of the relay device 620 receives an excrement detection signal through a communication device 624, the controller 624 may convert the corresponding signal into a packet structure suitable for communication with the user device 630, such that a signal received from the excrement alarming apparatus 610 is transmitted to the user device 630.

An application provided in the user device 630 may provide information received from the excrement alarming apparatus 610 to a user. In addition, when an excrement detection signal is received from the excrement alarming apparatus 610, the application 640 may immediately provide the excrement detection signal to a user.

Figure 7:
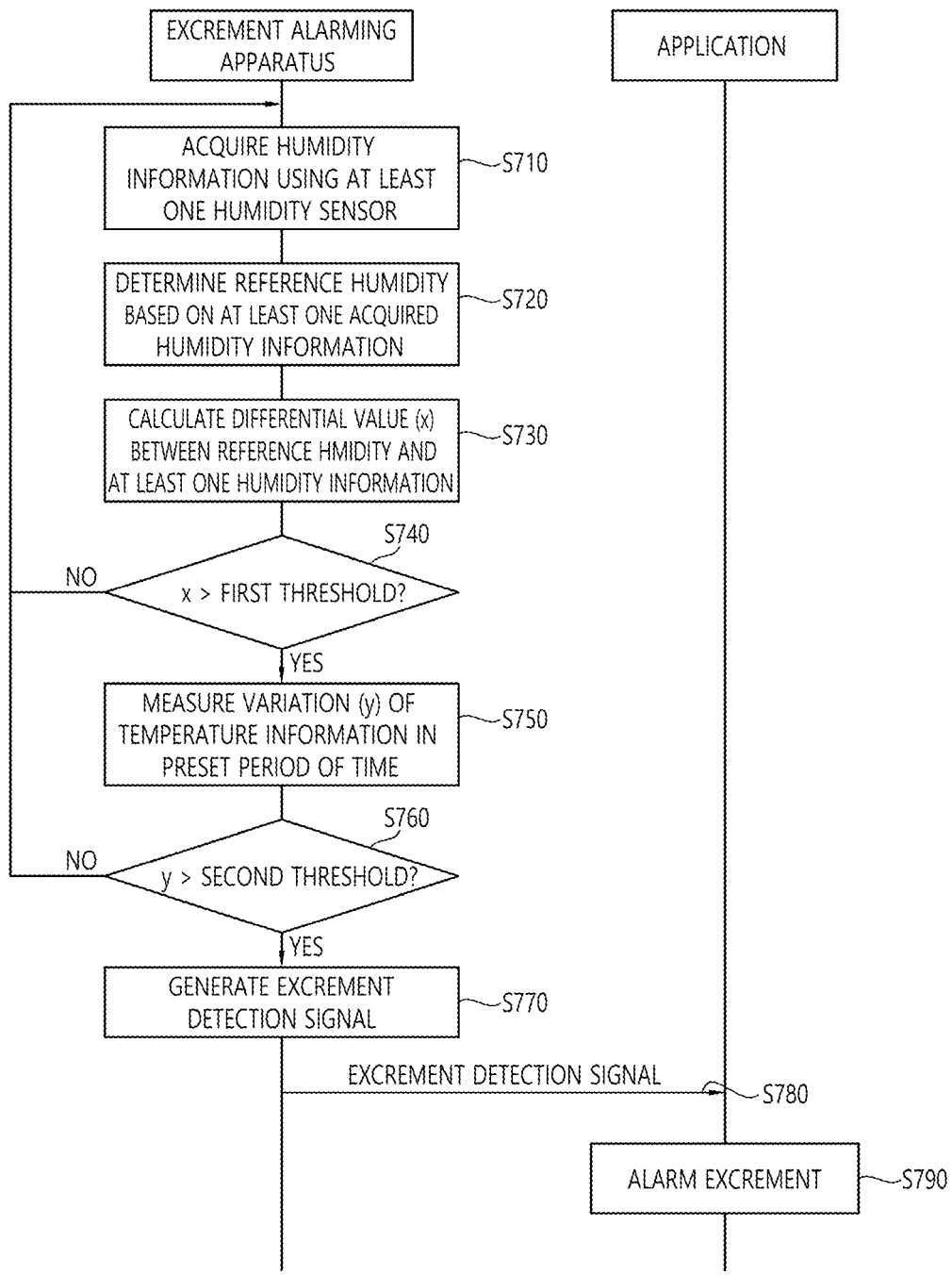
FIG. 7 is a flowchart illustrating an excrement alarming method according to another embodiment of the present invention.

FIG. 7 is a flowchart illustrating an excrement alarming method according to another embodiment of the present invention.

Hereinafter, a method for alarming excrement according to a third embodiment of the present invention is described with reference to FIG. 7.

An excrement alarming apparatus may periodically acquire humidity information using at least one humidity sensor (S710). In addition, the excrement alarming apparatus may determine reference humidity based on at least one humidity information (S720). When the excrement alarming apparatus includes only one humidity sensor, the excrement alarming apparatus may set an average value of humidity information measured by the corresponding humidity sensor within a preset period of time as reference humidity. If the excrement alarming apparatus includes a plurality of humidity sensors, humidity information of a diaper may be measured by a humidity sensor provided on one side of the excrement alarming apparatus and reference humidity may be determined using a humidity sensor provided on the other side of the excrement alarming apparatus.

When the reference humidity is determined, the excrement alarming apparatus may calculate a differential value x between information on the reference humidity and the at least one humidity information (S730), and compare the differential value x with a first threshold value (S740). When the differential value x is greater than the first threshold value, the excrement alarming apparatus may measure a variation y of temperature information measured by a temperature sensor within a preset period of time (S750), and compare the variation y with a second threshold value (S760). When the variation y is greater than the second threshold value, the excrement alarming apparatus may determine that excrement is detected, and may generate an excrement detection signal (S760). The generated excrement detection signal may be constructed in a packet structure as illustrated in FIG. 2, and transmitted to the application. When the excrement detection signal is received, the application may provide an excrement alarm through the user device (S790).

The foregoing description is merely illustrative of the technical features of the present disclosure, and various modifications and variations can be made by those having ordinary skill in the art without departing from the essential characteristics of the present disclosure. Therefore, the embodiments disclosed herein are not intended to limit but to illustrate the technical features of the present disclosure, and the scope of the technical features of the present disclosure is not limited by these embodiments. The scope of the present disclosure should be construed according to the appended claims, and all technical features falling within its equivalent scope should be construed as being included in the scope of the present disclosure.

According to the present invention, it is possible to more accurately detect excrement regardless of a change in a surrounding environment and effectively reduce power consumption of the excrement alarming apparatus.

What is claimed is:

1. An excrement alarming method implemented by an excrement alarming apparatus, the method comprising:
generating first humidity information using a humidity sensor provided on one side of the excrement alarming apparatus, and receiving second humidity information from an external device;
comparing a differential value between the first humidity information and the second humidity information with a first threshold value;
when the differential value between the first humidity information and the second humidity information is greater than the first threshold value, comparing a variation of temperature information measured by a temperature sensor, which is provided on one side of the excrement alarming apparatus, within a preset period of time with a second threshold value; and when the variation of the temperature information is greater than the second threshold value, transmit an excrement detection signal indicating that excrement is detected.

2. The excrement alarming method of claim 1, wherein the second humidity information is determined based on location information of the external device or measured by a humidity sensor provided in the external device.

3. The excrement alarming method of claim 1, wherein the second humidity information is received from the external device.

4. The excrement alarming method of claim 1, further comprising, before the determining, setting a weight for at least one of the first threshold value or the second threshold value based on at least one of date information or time information.

5. An excrement alarming method implemented by a user device, the method comprising:
- receiving temperature information and humidity information from an excrement alarming apparatus;
- determining reference humidity based on at least one of the humidity information or information acquired from the user device; and
- when excrement is detected based on the temperature information, the humidity information, and information on the reference humidity, alarming the detection of excrement through the user device,
- wherein the reference humidity is an average value of a plurality of humidity information received from the excrement alarming apparatus within a preset period of time.

6. The excrement alarming method of claim 5, further comprising:
- acquiring at least one of the temperature information and the humidity information from the excrement alarming apparatus.

7. The excrement alarming method of claim 5, further comprising:
- transmitting the information on the reference humidity to the excrement alarming apparatus.

8. An excrement alarming method implemented by a user device, the method comprising:
- receiving temperature information and humidity information from an excrement alarming apparatus;
- determining reference humidity based on at least one of the humidity information or information acquired from the user device; and
- when excrement is detected based on the temperature information, the humidity information, and information on the reference humidity, alarming the detection of excrement through the user device,
- wherein the alarming comprises:
  - comparing a differential value between the humidity information and the information on the reference humidity with a first threshold value;
  - when the differential value between the humidity information and the information on the reference humidity is greater than the first threshold value, comparing a variation of temperature information measured within a preset period of time with a second threshold value; and
  - when the variation of the temperature information is greater than the second threshold value, determining that excrement is detected.

9. The excrement alarming method of claim 8, further comprising:
- setting a weight for at least one of the first threshold value or the second threshold value based on at least one of the information on the reference humidity, location information, date information, weather information, or time information.

* * * * *